United States Patent
Behler et al.

(10) Patent No.: US 10,370,618 B2
(45) Date of Patent: Aug. 6, 2019

(54) AQUEOUS SURFACTANT COMPOSITIONS

(71) Applicant: BASF SE, Ludwigshafen (DE)

(72) Inventors: Ansgar Behler, Bottrop (DE); Claudia Brunn, Duesseldorf (DE); Detlev Stanislowski, Mettmann (DE)

(73) Assignee: BASF SE, Ludwigshafen (DE)

( * ) Notice: Subject to any disclaimer, the term of this patent is extended or adjusted under 35 U.S.C. 154(b) by 160 days.

(21) Appl. No.: 15/505,623

(22) PCT Filed: Aug. 7, 2015

(86) PCT No.: PCT/EP2015/068291
§ 371 (c)(1),
(2) Date: Feb. 22, 2017

(87) PCT Pub. No.: WO2016/030172
PCT Pub. Date: Mar. 3, 2016

(65) Prior Publication Data
US 2017/0283741 A1     Oct. 5, 2017

(30) Foreign Application Priority Data

Aug. 27, 2014 (EP) .................... 14182366

(51) Int. Cl.
| | | |
|---|---|---|
| A61K 8/23 | (2006.01) | |
| C11D 1/10 | (2006.01) | |
| A61K 8/46 | (2006.01) | |
| C11D 1/28 | (2006.01) | |
| C11D 1/37 | (2006.01) | |
| C11D 3/00 | (2006.01) | |
| C11D 11/00 | (2006.01) | |
| A61K 8/44 | (2006.01) | |
| A61Q 5/02 | (2006.01) | |
| A61Q 19/10 | (2006.01) | |
| A61K 8/36 | (2006.01) | |
| A61Q 9/02 | (2006.01) | |
| A61Q 11/00 | (2006.01) | |

(52) U.S. Cl.
CPC .............. *C11D 1/10* (2013.01); *A61K 8/23* (2013.01); *A61K 8/361* (2013.01); *A61K 8/44* (2013.01); *A61K 8/466* (2013.01); *A61Q 5/02* (2013.01); *A61Q 9/02* (2013.01); *A61Q 11/00* (2013.01); *A61Q 19/10* (2013.01); *C11D 1/28* (2013.01); *C11D 1/37* (2013.01); *C11D 3/0094* (2013.01); *C11D 11/0023* (2013.01); *A61K 2800/262* (2013.01); *A61K 2800/596* (2013.01)

(58) Field of Classification Search
None
See application file for complete search history.

(56) References Cited

U.S. PATENT DOCUMENTS

2012/0208898 A1* 8/2012 Dong ................ A61K 8/20
514/785

FOREIGN PATENT DOCUMENTS

| DE | 4009096 A1 | 9/1991 |
|---|---|---|
| EP | 2468842 A1 | 6/2012 |

OTHER PUBLICATIONS

Schambil, F., et al., "Physico-Chemical Properties of α-Sulphoto Fatty Acid Methyl Esters and α-Sulpho Fatty Acid Di-Salts." *Tenside, Surfactants, Detergents* 27, No. 6 (1990), pp. 380-385.
Su, E.G., et al., "Formulating »Sulfate-Free«, Mild Personal Cleansing Products with Amino Acid-Based Surfactants." *SOFW Journal* 139 (Apr. 2013), pp. 30-36.
International Search Report for International Patent Application No. PCT/EP2015/068291, dated Oct. 14, 2015.

* cited by examiner

*Primary Examiner* — Nannette Holloman
(74) *Attorney, Agent, or Firm* — Marshall, Gerstein & Borun LLP

(57) ABSTRACT

Aqueous surfactant compositions containing
one or more alpha-sulfo fatty acid disalts (A) of the general formula (I),

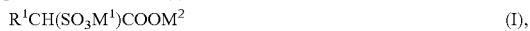

$$R^1CH(SO_3M^1)COOM^2 \qquad (I),$$

in which the radical $R^1$ is a linear or branched alkyl or alkenyl radical with 6 to 18 carbon atoms and the radicals $M^1$ and $M^2$, independently of one another, are selected from the group H, Li, Na, K, Ca/2, Mg/2, ammonium and alkanolamines, one or more N-acylglutamic acid compounds (B) of the general formula (II),

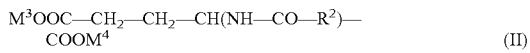

$$M^3OOC-CH_2-CH_2-CH(NH-CO-R^2)-COOM^4 \qquad (II)$$

in which the radical $R^2$ is a linear or branched alkyl or alkenyl radical with 7 to 19 carbon atoms and the radicals $M^3$ and $M^4$, independently of one another, are selected from the group H, Li, Na, K, Ca/2, Mg/2, ammonium and alkanolamines, and
water,
with specific limiting conditions, are disclosed. The compositions are transparent, storage-stable, exhibit good foaming ability, and are suitable for cosmetic products, detergents, and cleaners.

15 Claims, No Drawings

AQUEOUS SURFACTANT COMPOSITIONS

CROSS-REFERENCE TO RELATED APPLICATIONS

This is the U.S. national phase of International Application No. PCT/EP2015/068291, filed Aug. 7, 2015, which claims the benefit of European Patent Application No. 14182366.6, filed Aug. 27, 2014.

FIELD OF THE INVENTION

The present invention relates to aqueous surfactant compositions with a content of alpha-sulfo fatty acid disalts and specific N-acylglutamic acid compounds.

PRIOR ART

Anionic surfactants are some of the most widespread interface-active compounds and, apart from being used in detergents and cleaners, are also used for diverse purposes in the field of cosmetics. Customary anionic surfactants as are used in particular in cosmetics are the salts of alkyl ether sulfates (alkyl polyether sulfates, fatty alcohol polyglycol ether sulfates, in short also ether sulfates). They are characterized by a strong foaming ability, high cleaning power, low sensitivity to hardness and grease and are used widely for producing cosmetic products such as, for example, hair shampoos, foam or shower baths, but also in hand dishwashing detergents.

For many current applications, apart from a good interface-active effect, further requirements are placed on anionic surfactants. A high dermatological compatibility is required in particular in cosmetics. Furthermore, an adequate solubility in water, good compatibility with as many as possible of the active ingredients and auxiliaries used in cosmetics, a good foaming ability and good thickenability are generally desired. Furthermore, there is a need for anionic surfactants which can be produced at least partially from biogenic sources and specifically also renewable raw materials. Furthermore, there is also a need for surfactants which have no alkoxylated groups and which thus render superfluous in particular the use of ethylene oxide for their production.

The so-called alpha-sulfo fatty acid disalts ("disalts") are a known class of surfactant but have a very poor solubility in water (cf. e.g. F. Schambil and M. J. Schwuger, Tenside Surf. Det. 27 (1990), 6, pp. 380-385): Thus, for example the solubility in water of C14-di-Na salt at 20° C. is only 0.7% (compare the graph on p. 381). This is unsatisfactorily low for practice, for example cosmetic preparations. Accordingly, disalts have not hitherto been used in aqueous surfactant formulations as anionic base surfactant and have not been used for preparing transparent, stable formulations due to their poor water solubility.

E. G. Su et al. (SÖFW Journal 139 4-2013, pages 30 and 32-36) describe formulations comprising sulfate-free skin-mild cleansing compositions comprising amino acid-based surfactants. Three types of amino acid-based surfactants are investigated here, namely glycinates, sarcosinates and glutamates. The investigation comes to the conclusion that these three types of surfactants are suitable as substitutes for lauryl ether sulfates in cleansing compositions. The glycinates are the focus of the article while the glutamates are only generally mentioned. A potential combination of glutamates with alpha-sulfo fatty acid disalts is not disclosed.

Investigations by the applicant have shown that the foaming ability of amino acid-based surfactants, particularly N-acylglutamates, is highly pH dependent and is inadequate over broad pH ranges for cosmetic rinse-off formulations. Rinse-off formulations are understood to mean formulations for shower baths, hair shampoos and the like, which depend on good foaming behavior, in particular excellent initial foaming behavior, and where rinsing off the skin takes place after use.

Investigations by the applicant have also shown that amino acid-based surfactants, particularly N-acylglutamates, can only be incorporated with difficulty in stable, transparent formulations at low pH.

DESCRIPTION OF THE INVENTION

The complex object of the present invention was to provide aqueous surfactant compositions which are characterized by the properties specified below, with each of these properties constituting a technical feature:

Good transparency, which for the purposes of the present invention is to be understood as meaning that the aqueous surfactant compositions upon quantitative determination by means of a TurbiScan MA 2000 (measuring instrument from Formulaction) at 23° C. have an average transmission of at least 80%, preferably of at least 85% and in particular of at least 88%.

Good foaming ability. In this regard, it may be noted that in the field of cosmetics, foaming ability can be understood to mean different aspects, it being possible to use in particular foam volume, foam stability, foam elasticity, water content of the foam, optical features of the foam, for example, the pore size, and also the foam sensorics for the purposes of assessing the foam. It is particularly desirable for a surface-active formulation to have a high foam volume during initial foaming. The initial foaming behavior plays a very important role, particularly in so-called rinse-off products, which are to be understood as meaning products which come into contact with the skin during cleaning or grooming, but are then washed off again (e.g. shower gels, shower formulations, shampoos, liquid soaps, etc.). In this sector especially, as large a foam volume as possible is desired. In practice, the initial foaming takes place within a relatively short period (from a few seconds to one minute). Typically, during initial foaming, a shower gel or a shampoo is spread and caused to foam by rubbing between hands, skin and/or hair. An excellent initial foaming behavior is of fundamental importance in the context of the present invention. In the laboratory, the initial foaming behavior of an aqueous surfactant solution can be assessed e.g. by agitating the solution within a comparatively short time period by means of stirring, shaking, pumping, bubbling through a gas stream or in another way. The foam test used for the purposes of the present invention is described in more detail in the experimental section.

Hydrolysis stability at pHs of 8 or less.

Shelf life at room temperature (23° C.) over at least 12 weeks without any visible changes (for example clouding, discoloration, phase separation, loss of transparency and the like) arising.

The invention firstly provides aqueous surfactant compositions comprising
one or more alpha-sulfo fatty acid disalts (A) of the general formula (I), $$R^1CH(SO_3M^1)COOM^2 \qquad (I),$$

in which the radical $R^1$ is a linear or branched alkyl or alkenyl radical with 6 to 18 carbon atoms and the radicals $M^1$ and $M^2$—independently of one another—are selected from the group H, Li, Na, K, Ca/2, Mg/2, ammonium and alkanolamines, one or more N-acylglutamic acid compounds (B) of the general formula (II),

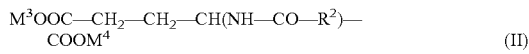

$$M^3OOC\text{—}CH_2\text{—}CH_2\text{—}CH(NH\text{—}CO\text{—}R^2)\text{—}COOM^4 \quad (II)$$

in which the radical $R^2$ is a linear or branched alkyl or alkenyl radical with 7 to 19 carbon atoms and the radicals $M^3$ and $M^4$—independently of one another—are selected from the group H, Li, Na, K, Ca/2, Mg/2, ammonium and alkanolamines water, where the following provisos apply:

the content of the compounds (A) and (B) in the aqueous surfactant compositions is—based on the total aqueous surfactant composition—at least 5% by weight;

if the aqueous surfactant compositions comprise one or more ester sulfonates (E) of the general formula (V),

$$R^5CH(SO_3M^7)COOR^6 \quad (V)$$

in which the radical $R^5$ is a linear or branched alkyl or alkenyl radical with 6 to 18 carbon atoms and the radical $R^6$ is a linear or branched alkyl or alkenyl radical with 1 to 20 carbon atoms, where the radical $R^6$ can logically be an alkenyl radical or be branched only above 3 carbon atoms, and the radical $M^7$ is selected from the group Li, Na, K, Ca/2, Mg/2, ammonium and alkanolamines, it is the case that the compounds (A)—based on the totality of the compounds (A) and (E)—must be present to 50% by weight or more—and in particular to 90% by weight or more;

the weight ratio of the compounds (B):(A) in the aqueous surfactant compositions is in the range from 2:1 to 6:1;

the pH of the aqueous surfactant compositions is 8 or less;

the average transmission of the aqueous surfactant compositions at 23° C.—measured using a TurbiScan MA 2000—is at least 80%.

Surprisingly, the aforementioned complex object was achieved in an excellent manner by the surfactant compositions according to the invention. It was unforeseeable and therefore highly surprising that disalts (A) can be used in combination with the N-acylglutamic acid compounds (B) in considerably higher concentrations, evident from the fact that the aqueous compositions are transparent and not cloudy. In other words: The solubility of the disalts (A) undergoes a significant increase by the combination with the N-acylglutamic acid compounds (B). The compositions according to the invention also show a synergistic foaming behavior: whereas both surfactants individually have a less satisfactory foaming behavior for the rinse-off range of application, the inventive combinations of the surfactants (A) and (B) show an excellent initial foaming behavior.

The Compounds (A)

The compounds (A), which are referred to within the context of the present invention as alpha-sulfo fatty acid disalts, are obligatory for the aqueous surfactant compositions according to the invention. They have the aforementioned formula (I)

$$R^1CH(SO_3M^1)COOM^2 \quad (I),$$

in which the radical $R^1$ is a linear or branched alkyl or alkenyl radical with 6 to 18 carbon atoms and the radicals $M^1$ and $M^2$—independently of one another—are selected from the group H, Li, Na, K, Ca/2, Mg/2, ammonium and alkanolamines. In this connection, particularly preferred alkanolamines are monoethanolamine, diethanolamine, triethanolamine and monoisopropanolamine.

In one embodiment, the proviso applies that the fraction of the compounds (A) in the aqueous surfactant compositions in which the radical $R^1$ is an alkenyl radical—based on the total amount of the compounds (A)—is 3% by weight or less.

In a preferred embodiment, the radical $R^1$ in the formula (I) is a saturated, linear radical with 10 to 16 carbon atoms, where with regard to the compounds (A) it is the case that the fraction of the compounds (A) in which the radical $R^1$ is a decyl and/or a dodecyl radical—based on the total amount of the compounds (A)—is 90% by weight or more.

Preferably, the radicals $M^1$ and $M^2$ in the formula (I) are Na.

The compounds (A) can be prepared by all methods known appropriately to the person skilled in the art. A particularly preferred method of preparation here is the sulfation of the corresponding carboxylic acids. Here, the corresponding carboxylic acid and in particular the corresponding fatty acids are reacted with gaseous sulfur trioxide, the sulfur trioxide being used preferably in an amount such that the molar ratio of $SO_3$ to fatty acid is in the range from 1.0:1 to 1.1:1. The crude products obtained in this way, which are acidic sulfation products, are then partially or completely neutralized, preference being given to complete neutralization with aqueous NaOH. If desired, it is also possible to undertake purification steps and/or a bleaching (for adjusting the desired pale color of the products).

In a particularly preferred embodiment, the compounds (A) are used in technical-grade form. This means that the corresponding carboxylic acids, in particular native fatty acid, are sulfated with gaseous sulfur trioxide, as a result of which, following partial or complete neutralization of the resulting acidic sulfation products, a mixture of the compounds (A), (C) and (D) results. By virtue of corresponding adjustments of the reaction parameters (in particular molar ratio of carboxylic acid and sulfur trioxide, and also reaction temperature) it is possible to control the ratio of the compounds (A), (C) and (D). The compounds (C) and (D) are described below in the chapter "Preferred embodiments".

Within the context of the present invention, preference is given to those technical-grade mixtures of the alpha-sulfo fatty acid disalts which have the following composition:

the content of (A) is in the range from 60 to 100% by weight, the content of (C) is in the range from 0 to 20% by weight, the content of (D) is in the range from 0 to 20% by weight, with the proviso that the sum of the components (A), (C) and (D) in this mixture is 100% by weight.

Very particular preference is given to those technical-grade mixtures which are composed as follows:

the content of (A) is in the range from 70 to 80% by weight, the content of (C) is in the range from 10 to 15% by weight, the content of (D) is in the range from 10 to 15% by weight, with the proviso that the sum of the components (A), (C) and (D) in this mixture is 100% by weight.

The Compounds (B)

The compounds (B), which are referred to in the context of the present invention as N-acylglutamic acid compounds, are obligatory for the aqueous surfactant compositions according to the invention. They have the aforementioned formula (II)

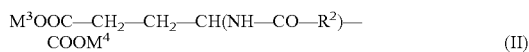

in which the radical $R^2$ is a linear or branched alkyl or alkenyl radical with 7 to 19 carbon atoms and the radicals $M^3$ and $M^4$—independently of one another—are selected from the group H, Li, Na, K, Ca/2, Mg/2, ammonium and alkanolamines. In this connection, particularly preferred alkanolamines are monoethanolamine, diethanolamine, triethanolamine and monoisopropanolamine. In one embodiment, the radicals $M^3$ and $M^4$ are both Na (sodium).

In one embodiment, the proviso applies that the fraction of the compounds (B) in which the radical $R^2$ is an alkenyl radical—based on the total amount of the compounds (B) in the aqueous surfactant compositions—is 3% by weight or less.

The compounds (B) can be prepared by all of the methods known appropriately to the person skilled in the art.

In one embodiment, the radical $R^2$ in the formula (II) is a saturated, linear radical with 11 to 13 carbon atoms.

PREFERRED EMBODIMENTS

In one embodiment, the aqueous surfactant compositions according to the invention comprise, besides the compounds (A), (B) and water, additionally one or more compounds (C) of the general formula (III)

In the formula (III), the radical $R^4$ is a linear or branched alkyl or alkenyl radical with 7 to 19 carbon atoms and the radicals $M^5$ is selected from the group H, Li, Na, K, Ca/2, Mg/2, ammonium and alkanolamines. In this connection, particularly preferred alkanolamines are monoethanolamine, diethanolamine, triethanolamine and monoisopropanolamine.

In one embodiment, the aqueous surfactant compositions according to the invention comprise, besides the compounds (A), (B) and water, additionally one or more inorganic salts of sulfuric acid (D) of the general formula (IV)

wherein $M^6$ is selected from the group Li, Na, K, Ca/2, Mg/2, ammonium and alkanolamine. In this connection, particularly preferred alkanolamines are monoethanolamine, diethanolamine, triethanolamine and monoisopropanolamine.

In a preferred embodiment, the aqueous surfactant compositions according to the invention comprise the compounds (A), (B), (C) and (D). Here, it is particularly preferred if the radicals $M^1$ and $M^2$ of the compounds (A), the radicals $M^3$ and $M^4$ of the compounds (B), the radical $M^5$ of the compounds (C) and the radical $M^6$ of the compounds (D) are Na (sodium).

As explained above, the content of the compounds (A) and (B) in the compositions—based on the total composition—is at least 5% by weight. Preferably, the content of the compounds (A) and (B) in the compositions—based on the total composition—is in the range from 5 to 50% by weight, in particular in the range from 5 to 20% by weight and particularly preferably in the range from 8 to 12% by weight.

As stated above, the weight ratio of the compounds (B):(A) in the compositions is in the range from 2:1 to 6:1.

In a preferred embodiment, the weight ratio of the compounds (B):(A) in the compositions is in the range from 3:1 to 4.5:1.

The pH of the compositions is 8 or less. The pH is preferably adjusted to 7 or less. In a preferred embodiment, the pH of the compositions is in the range from 4.5 to 7.0 and particularly 4.5 to 5.5.

If desired, the aqueous surfactant compositions according to the invention can additionally comprise one or more further surfactants which, in structural terms, do not belong to the aforementioned compounds (A), (B), (D) or (E). These surfactants may be anionic, cationic, nonionic or amphoteric surfactants.

Use of the Compositions

A further subject matter of the invention is the use of the aforementioned compositions for cosmetic products, and also detergents and cleaners.

With regard to cosmetic products, particular preference is given here especially to those which are present in the form of hair shampoos, shower gels, soaps, syndets, washing pastes, washing lotions, scrub preparations, foam baths, oil baths, shower baths, shaving foams, shaving lotions, shaving creams and dental care products (for example toothpastes, mouthwashes and the like).

With regard to cleaners, of preference here are in particular products with a low pH for cleaning hard surfaces, such as bath and toilet cleaners and the like, and also for cleaning and/or fragrance gels for use in sanitary installations.

EXAMPLES

Substances Used

Completely demin. water=completely demineralized water

SFA-I: alpha-sulfo fatty acid disalt of technical grade based on native $C_{12/14}$-fatty acid; composition: 74% by weight disodium 2-sulfolaurate, 13% by weight sodium laurate, 11% by weight sodium sulfate, 2% by weight water. The term "laurate" here means that the $C_{12/14}$ weight ratio of the mixture of the underlying native fatty acids is 70:30.

SFA-II: purified alpha-sulfo fatty acid disalt based on native $C_{12/14}$-fatty acid; composition: 90% by weight disodium 2-sulfolaurate, 5% by weight sodium laurate, 0.2% by weight sodium sulfate, 4.8% by weight water. The term "laurate" here means that the $C_{12/14}$ weight ratio of the mixture of the underlying native fatty acids is 70:30.

ACG: Plantapon ACG HC (sodium cocoyl glutamate, 41% by weight active substance), commercial product from BASF PCN).

Measurement and Test Methods pH: Using a standard commercial pH meter, the pH was measured directly in the formulation, i.e. the aqueous surfactant composition.

Homogeneity and appearance: Assessment of the homogeneity and appearance of the aqueous surfactant compositions was carried out visually (with the naked eye) in 125 ml wide-neck glass bottles. The homogeneity was assessed first here. In the context of the present invention, homogeneity is understood as meaning that no creaming visible to the naked eye or a sediment arises. If the compositions were assessed as homogeneous, their appearance was also assessed and characterized for example with attributes such as slightly opaque (but always still clearly translucent) to water-clear.

Transparency:

The samples were initially observed with the naked eye. Obvious cloudiness, crystals or sediments are directly recognized in this case. If the sample was evidently free of solid precipitates, the transparency was determined quantitatively by means of a TurbiScan MA 2000 (measuring instrument from Formulaction) at 23° C. The samples were designated as transparent if they had a mean transmission of at least 80%. Accordingly, the description "transparent" in Table 1 below means that the mean transmission was at least 80%.

For the quantitative determination of the transparency using a TurbiScan MA 2000, firstly 5 ml samples of the aqueous surfactant compositions to be tested were placed into the instrument-specific measuring cell and left to stand for 24 hours at room temperature (23° C.) until all of the air bubbles had escaped. Then, the transmission of the incident light (wavelength 850 nm) was measured over a sample level from 20 mm to 50 mm. The evaluation was carried out using the Turbisoft software (Version 1.2.1.) supplied by the manufacturer of the measuring instrument: for each measurement, an average value of the transmission (in %) above the sample level is output by the software. This average value is called average transmission for the purposes of the present application. Here, the transmission measurement was repeated 3 times for each sample and the numerical average value was formed from the resulting values for the average transmission.

Determination of the Initial Foaming Behavior:

To test the initial foaming behavior (rotor foam method), a standard commercial measuring instrument was used (Sita Foam Tester R 2000). For this, an aqueous surfactant solution was firstly prepared as follows: 1 g of active substance of each sample to be tested (the samples used were SFA-I or ACG or mixtures of these substances, see below; in the case of SFA-I, active substance content is understood—as stated above—as meaning the disalt content) was dissolved at 20° C. in 1 liter of completely demineralized water (=water with a degree of hardness of 0° German hardness). The pH of the solution was adjusted to the desired value with dilute citric acid or aqueous sodium hydroxide solution—the respective value is given in Tables 1 and 2. The solution prepared in this way was heated to 30° C.

250 ml of the heated reservoir were transferred to the measuring instrument and foamed at a speed of 1300 revolutions per minute for 10 seconds, the foam volume then present was ascertained (in ml), then foamed for a further 10 seconds, the foam volume then present was ascertained (in ml), etc., i.e. the foam level was determined every 10 seconds during foaming.

After a foaming time of 80 seconds, the measurement was ended. The measurement was repeated for each sample 3 times, in each case using a fresh solution from the same batch, and the result of the measurements after 40, 60 and 80 seconds was given as an average from these three measurements (see table).

Shelf Life:

The surfactant compositions were stored at 23° C. for a period of 12 weeks. Then, the testing of the two parameters homogeneity and appearance of the compositions was carried out. The compositions were then considered to be storage-stable if both parameters remained unchanged over the entire period of 12 weeks.

EXAMPLES

Example 1 (Inventive)

Preparation (batch size 200 g): The components according to Table 1 were dissolved in completely demineralized water at 23° C. with stirring (completely demineralized water=water with a degree of hardness of 0° German hardness). The pH was then adjusted to the value stated in Table 1 by addition of citric acid (50% solution). The assessed parameters (homogeneity, appearance, shelf life) can be found in Table 1.

Example 2 (Inventive)

Preparation as example 1, but with changed amounts of the components used (see Table 1). pH adjustment as in Example 1 with citric acid (to the value given in Table 1). The assessed parameters (homogeneity, appearance, shelf life) can be found in Table 1.

TABLE 1

|  | Example 1 | Example 2 |
|---|---|---|
| ACG | 43.9 g | 47.9 g |
| SFA I | 8.1 g | 5.9 g |
| Completely demin. water | 148.0 g | 146.2 g |
| pH | 4.6 | 4.6 |
| Homogeneity | homogeneous | homogeneous |
| Appearance | transparent | transparent |
| Shelf life | stable | stable |
| Active substance content | 12% | 12% |
| Weight ratio Active substance ACG:SFA I | 3:1 | 4.5:1 |

Comparative Examples 1 and 2

Preparation as example 1, but ACG or SFA I was used exclusively (see Table 2). pH was adjusted with citric acid (to the value given in Table 2). The assessed parameters (homogeneity, appearance, shelf life) can be found in Table 2.

TABLE 2

|  | Comparative Example 1 | Comparative Example 2 |
|---|---|---|
| ACG | 43.9 g |  |
| SFA I |  | 32.4 g |
| Completely demin. water | 156.1 g | 167.6 g |
| pH | 4.6 | 4.5 |
| Homogeneity | inhomogeneous | inhomogeneous |
| Appearance | white, crystalline sediment | white sediment |
| Active substance content | 9% | 6% |
| Weight ratio Active substance ACG:SFA I | 1:0 | 0:1 |

Examples 3 to 7 (Inventive)

The data on the initial foaming behavior of surfactant mixtures ACG/SFA I or ACG/SFA II can be taken from Table 3.

TABLE 3

|  | Example 3 | Example 4 | Example 5 | Example 6 | Example 7 |
|---|---|---|---|---|---|
| ACG | 1.83 g | 1.95 g | 1.95 g | 1.99 g | 1.99 g |
| SFA I | 0.34 g | 0.27 g | 0.27 g | 0.24 g |  |
| SFA II |  |  |  |  | 0.20 g |

TABLE 3-continued

|  | Example 3 | Example 4 | Example 5 | Example 6 | Example 7 |
|---|---|---|---|---|---|
| Weight ratio Active substance ACG:SFA | 3:1 | 4:1 | 4:1 | 4.5:1 | 4.5:1 |
| Completely demin. water | 1000 ml | 1000 ml | 1000 ml | 1000 ml | 1000 ml |
| pH | 5.5 | 4.0 | 5.0 | 6.9 | 5.5 |
| Foam volume after 40 sec | 426 ml | 597 ml | 480 ml | 391 ml | 477 ml |
| Foam volume after 60 sec | 672 ml | 835 ml | 808 ml | 543 ml | 794 ml |
| Foam volume after 80 sec | 854 ml | 851 ml | 869 ml | 746 ml | 857 ml |

Comparative Examples 3 to 7

The data on the initial foaming behavior of the individual surfactants ACG or SFA I can be taken from Table 4.

TABLE 4

|  | Comparative example 3 | Comparative example 4 | Comparative example 5 | Comparative example 6 | Comparative example 7 |
|---|---|---|---|---|---|
| ACG | 2.44 g | 2.44 g | 2.44 g |  |  |
| SFA I |  |  |  | 1.35 g | 1.35 g |
| Weight ratio Active substance ACG:SFA | 1:0 | 1:0 | 1:0 | 0:1 | 0:1 |
| Completely demin. water | 1000 ml | 1000 ml | 1000 ml | 1000 ml | 1000 ml |
| pH | 4.0 | 5.5 | 7.0 | 5.5 | 7.0 |
| Foam volume after 40 sec | 205 ml | 201 ml | 110 ml | 148 ml | 271 ml |
| Foam volume after 60 sec | 261 ml | 285 ml | 166 ml | 188 ml | 369 ml |
| Foam volume after 80 sec | 304 ml | 365 ml | 232 ml | 215 ml | 460 ml |

The invention claimed is:

1. An aqueous surfactant composition comprising
one or more alpha-sulfo fatty acid disalt (A) of general formula (I), $$R^1CH(SO_3M^1)COOM^2 \quad (I)$$

in which the radical $R^1$ is a linear or branched alkyl or alkenyl radical with 6 to 18 carbon atoms and the radicals $M^1$ and $M^2$, independently of one another, are selected from the group H, Li, Na, K, Ca/2, Mg/2, ammonium, and alkanolamine,
one or more N-acylglutamic acid compound (B) of general formula (II), $$M^3OOC—CH_2—CH_2—CH(NH—CO—R^2)—COOM^4 \quad (II)$$

in which the radical $R^2$ is a linear or branched alkyl or alkenyl radical with 7 to 19 carbon atoms and the radicals $M^3$ and $M^4$, independently of one another, are selected from the group H, Li, Na, K, Ca/2, Mg/2, ammonium, and alkanolamines, and
water,
where the following provisos apply:
a content of the compounds (A) and (B) in the aqueous surfactant composition is, based on the total aqueous surfactant composition, at least 5% by weight;
if the aqueous surfactant composition comprises one or more ester sulfonate (E) of general formula (V), $$R^5CH(SO_3M^7)COOR^6 \quad (V)$$

in which the radical $R^5$ is a linear or branched alkyl or alkenyl radical with 6 to 18 carbon atoms and the radical $R^6$ is a linear or branched alkyl or alkenyl radical with 1 to 20 carbon atoms, where the radical $R^7$ is an alkenyl radical or is branched only above 3 carbon atoms, and the radical $M^7$ is selected from the group Li, Na, K, Ca/2, Mg/2, ammonium, and alkanolamines, the compounds (A), based on the totality of the compounds (A) and (E), must be present to 50% by weight or more;
the weight ratio of the compounds (B):(A) in the aqueous surfactant composition is in the range from 2:1 to 6:1;
the pH of the aqueous surfactant composition is 8 or less;
the average transmission of the aqueous surfactant composition at 23° C.—measured using a TurbiScan MA 2000—is at least 80%.

2. The composition according to claim 1, wherein the radical $R^2$ in the formula (II) is a saturated alkyl radical with 11 to 13 carbon atoms.

3. The composition according to claim 1, wherein the radical $R^1$ in the formula (I) is a saturated, linear radical with 10 to 16 carbon atoms, wherein for compound (A), the fraction of the compound (A) in which the radical $R^1$ is a decyl or a dodecyl radical, based on the total amount of the compounds (A), is 90% by weight or more.

4. The composition according to claim 1, wherein the radicals $M^1$ and $M^2$ are Na.

5. The composition according to claim 1, wherein the radicals $M^3$ and $M^4$ are Na.

6. The composition according to claim 1, wherein the composition comprises additionally one or more compound (C) of general formula (III)

$$R^4COOM^5 \quad (III)$$

in which the radical $R^4$ is a linear or branched alkyl or alkenyl radical with 7 to 19 carbon atoms and the radicals $M^5$ is selected from the group H, Li, Na, K, Ca/2, Mg/2, ammonium, and alkanolamine.

7. The composition according to claim 1, wherein the composition comprises additionally one or more inorganic salt of sulfuric acid (D) of the general formula (IV)

$$(M^6)_2SO_4 \quad (IV)$$

wherein $M^6$ is selected from the group Li, Na, K, Ca/2, Mg/2, ammonium, and alkanolamine.

8. The composition according to claim 1, wherein the content of the compounds (A) and (B) in the composition, based on the total composition, is in the range from 8 to 12% by weight.

9. The composition according to claim 1, wherein the weight ratio of the compounds (B):(A) in the composition is in the range from 3:1 to 4.5:1.

10. The composition according to claim 1, wherein the pH of the composition is in the range from 4.0 to 7.0.

11. The composition according to claim 1, wherein the pH of the composition is in the range from 4.5 to 5.5.

12. A cosmetic product comprising a composition of claim 1.

13. The cosmetic product of claim 12 in the form of hair shampoos, shower gels, soaps, syndets, washing pastes, washing lotions, scrub preparations, foam baths, oil baths, shower baths, shaving foams, shaving lotions, shaving creams, and dental care products.

14. A detergent or cleaner comprising a composition of claim 1.

15. The detergent or cleaner of claim 14 in the form of a hard surface cleaner, a bath cleaner, a toilet cleaner, or a fragrance gel.

\* \* \* \* \*